(12) United States Patent
Dolfi et al.

(10) Patent No.: US 9,011,148 B2
(45) Date of Patent: Apr. 21, 2015

(54) SURGICAL GUIDE SYSTEM FOR DENTAL IMPLANTOLOGY AND METHOD FOR MAKING THE SAME

(75) Inventors: Maurizio Dolfi, Florence (IT); Gabriele Scommegna, Florence (IT)

(73) Assignee: Leone S.p.A., Florence (IT)

( * ) Notice: Subject to any disclaimer, the term of this patent is extended or adjusted under 35 U.S.C. 154(b) by 12 days.

(21) Appl. No.: 14/128,806

(22) PCT Filed: Jun. 22, 2012

(86) PCT No.: PCT/IT2012/000194
§ 371 (c)(1),
(2), (4) Date: Dec. 23, 2013

(87) PCT Pub. No.: WO2013/005241
PCT Pub. Date: Jan. 10, 2013

(65) Prior Publication Data
US 2014/0193771 A1    Jul. 10, 2014

(30) Foreign Application Priority Data

Jul. 1, 2011   (IT) ................................ FI2011A0130

(51) Int. Cl.
| | |
|---|---|
| *A61C 3/00* | (2006.01) |
| *A61C 1/08* | (2006.01) |
| *A61C 3/02* | (2006.01) |
| *A61C 8/00* | (2006.01) |

(52) U.S. Cl.
CPC ................. *A61C 1/084* (2013.01); *A61C 1/085* (2013.01); *A61C 3/02* (2013.01); *A61C 8/0089* (2013.01)

(58) Field of Classification Search
USPC ................. 433/72–76, 215, 196, 213; 606/96
See application file for complete search history.

(56) References Cited

U.S. PATENT DOCUMENTS

| | | | | | |
|---|---|---|---|---|---|
| 5,015,183 | A | * | 5/1991 | Fenick | 433/76 |
| 5,133,660 | A | * | 7/1992 | Fenick | 433/76 |
| 5,320,529 | A | * | 6/1994 | Pompa | 433/76 |
| 5,556,278 | A | * | 9/1996 | Meitner | 433/75 |
| 5,718,579 | A | * | 2/1998 | Kennedy | 433/75 |
| 5,725,376 | A | * | 3/1998 | Poirier | 433/172 |
| 5,743,916 | A | * | 4/1998 | Greenberg et al. | 606/102 |
| 5,967,777 | A | * | 10/1999 | Klein et al. | 433/75 |

(Continued)

FOREIGN PATENT DOCUMENTS

| | | |
|---|---|---|
| EP | 2 189 130 A1 | 5/2010 |
| FR | 2 882 250 A1 | 8/2006 |

(Continued)

*Primary Examiner* — Cris L Rodriguez
*Assistant Examiner* — Hao D Mai
(74) *Attorney, Agent, or Firm* — McGlew and Tuttle, P.C.

(57) ABSTRACT

A surgical guide system for dental implantology has a plate (10) provided with a guide sleeve (2) delimiting a through hole with an axis oriented to a predetermined direction. A drill (4) for osteotomy has a spindle connected to a handpiece with drilling portion (41), the drill (4) being for association with the guide sleeve (2) during osteotomy. The diameter (d41) of the drilling head portion (41) is larger than the inner diameter (d2) of the guide sleeve (2) and the spindle is of smaller diameter, such that the association of the drill (4) to any of the guide sleeves (2) can be performed only by inserting the spindle through a gingival side of the sleeves. Upon association of the drill with the sleeve, the drilling head (41) protrudes from the gingival side (2G) thereof. The surgical guide has a void (100) accommodating the drilling head (41) of the drill.

2 Claims, 12 Drawing Sheets

(56) References Cited

U.S. PATENT DOCUMENTS

| | | | |
|---|---|---|---|
| 5,989,025 A * | 11/1999 | Conley | 433/76 |
| 6,319,000 B1 * | 11/2001 | Brånemark | 433/75 |
| 6,382,975 B1 * | 5/2002 | Poirier | 433/173 |
| 6,692,254 B1 * | 2/2004 | Kligerman et al. | 433/173 |
| 7,044,735 B2 * | 5/2006 | Malin | 433/75 |
| 7,086,860 B2 * | 8/2006 | Schuman et al. | 433/75 |
| 7,097,451 B2 * | 8/2006 | Tang | 433/76 |
| 7,322,821 B1 * | 1/2008 | Lin | 433/72 |
| 8,038,440 B2 * | 10/2011 | Swaelens et al. | 433/76 |
| 8,714,975 B2 * | 5/2014 | Stumpel | 433/75 |
| 8,794,963 B2 * | 8/2014 | Lancieux et al. | 433/75 |
| 2002/0102517 A1 * | 8/2002 | Poirier | 433/173 |
| 2002/0137003 A1 * | 9/2002 | Knapp | 433/76 |
| 2005/0170311 A1 * | 8/2005 | Tardieu et al. | 433/76 |
| 2006/0093988 A1 * | 5/2006 | Swaelens et al. | 433/76 |
| 2008/0124676 A1 * | 5/2008 | Marotta | 433/174 |
| 2009/0181340 A1 * | 7/2009 | Wolf et al. | 433/76 |
| 2009/0286197 A1 * | 11/2009 | Jamison | 433/75 |
| 2010/0124731 A1 * | 5/2010 | Groscurth et al. | 433/213 |
| 2010/0129768 A1 * | 5/2010 | Isidori | 433/75 |
| 2010/0185201 A1 * | 7/2010 | Kim | 606/80 |
| 2010/0240000 A1 | 9/2010 | Yau et al. | |
| 2011/0151399 A1 * | 6/2011 | De Clerck et al. | 433/75 |
| 2012/0135373 A1 * | 5/2012 | Cheng et al. | 433/75 |
| 2013/0023888 A1 * | 1/2013 | Choi et al. | 606/96 |

FOREIGN PATENT DOCUMENTS

| | | |
|---|---|---|
| JP | 2010 119 465 A | 6/2010 |
| KR | 100 993 666 B1 | 11/2010 |

* cited by examiner

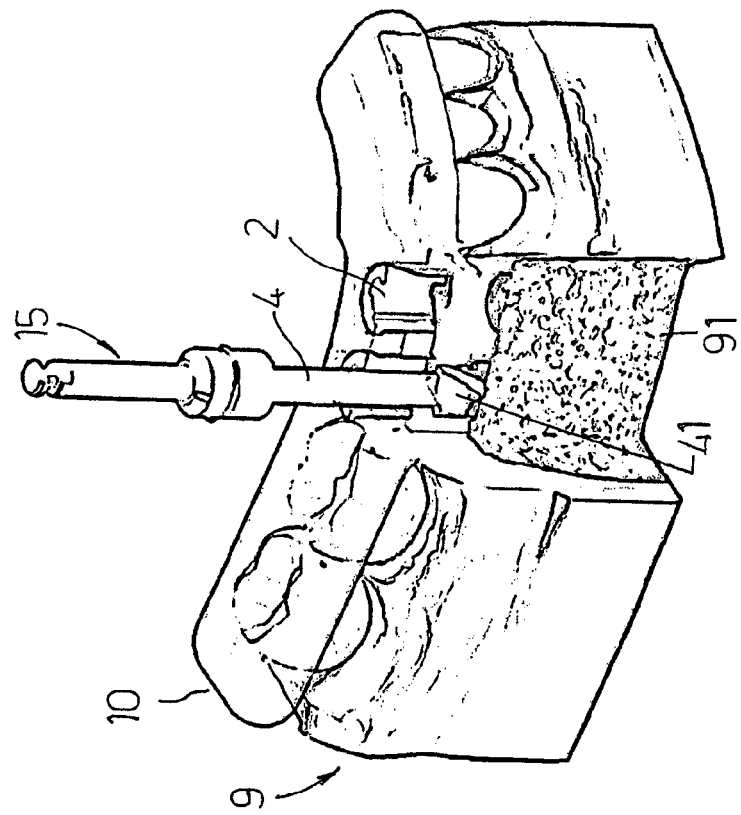
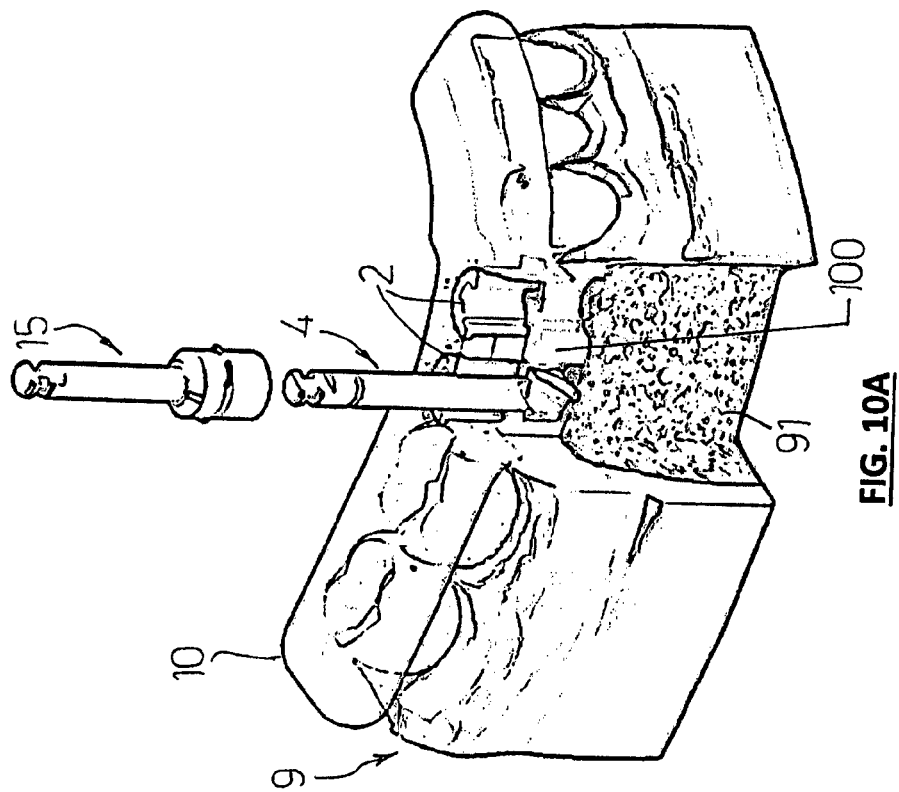

SURGICAL GUIDE SYSTEM FOR DENTAL IMPLANTOLOGY AND METHOD FOR MAKING THE SAME

The present invention relates to a system of surgical guide for dental implantology and a process for the production of surgical guides for dental implantation. It is known that, in dental surgery, a missing tooth can be replaced by a prosthetic tooth generally made of ceramic or other suitable material, applied on a dental implant, which is previously inserted into the jawbone of the patient. The dental implant must be properly oriented in the bone tissue and osseointegrated. The procedures usually adopted for this purpose include the execution of an osteotomy, i.e. the provision of a hole in the maxillary or mandibular bone, inserting the implant into the hole so practiced, and the subsequent attachment of the prosthetic tooth implant. The osteotomy is a particularly delicate stage of the procedure and must be located precisely at a proper distance from the adjacent teeth and must be properly oriented and of the right depth to not cause any damage to adjacent vital structures and to ensure the right set of prosthetic device with an acceptable result both from the functional point of view and from the aesthetic point of view. In an attempt to facilitate the location and drilling the hole in the maxillary or mandibular of the patient for the correct arrangement of the dental implant, techniques of various kinds, have been proposed as well as guidance systems which assist the physician in the execution of the osteotomy. In particular, the surgical guides for dental implantation are masks or plaques or templates made of plastic reproducing the dental arch and/or soft tissue of the oral cavity of the patient, including the edentulous areas in correspondence of which the implants must be positioned, provided with holes with suitably oriented tubular sleeves that guide the physician in the execution of the osteotomy and sometimes the actual positioning of the system. According to a known technique, such masks can be made by using CAD-CAM techniques based on computerized elaborations of the three-dimensional images of the bone concerned and of the underlying neural structures obtained by computerized axial tomography (TAC). In this way, the physician can intervene with greater accuracy by choosing the type of plant, the inclination and the depth on the basis of the actual state of the bone. Generally, the techniques of guided implantology provide for the positioning of a surgical guide on the arch concerned and the execution of the osteotomy that is practiced by using drills with a diameter appropriate to be inserted through the sleeves of the guide. The space available to perform the osteotomy in the mouth of the patient is, however, reduced by the encumbrance of the surgical guide limiting the operating stroke of the drill, and therefore limiting the depth of insertion of the implant into the bone, which in practice reduces the benefits arising from the use of the guide itself because a greater insertion depth of the implant in the available bone, corresponds to a higher stability of the system and consequently to a greater duration, unless the doctor decides to remove the template and operate without the aid of the latter thus giving up its benefits.

The main purpose of the present invention is to eliminate, or at least greatly reduce, the aforementioned drawbacks. Another object of the present invention is to allow adequate irrigation of the implant alveolus during osteotomy.

This result is achieved, according to the present invention, by adopting the idea of making a guide for dental implantation having the characteristics indicated in the independent claims. Other features of the present invention are the subject of the dependent claims.

Thanks to the present invention, it is possible to perform the osteotomy achieving a greater drilling depth compared to traditional surgical guides for dental implants, always ensuring the most correct orientation of the latter in the bone tissue concerned. Furthermore, the use of a surgical guide for dental implants in accordance with the present invention is particularly simple and can reduce the number of passages or strokes of the drill and the execution time of the intervention, with the shortest exposure of the bone, and improve accuracy. Further advantages derive the effective irrigation of the alveolus permitted by the present surgical guide for dental implantation.

These and other advantages and features of the present invention will be best understood by anyone skilled in the art thanks to the following description and the accompanying drawings, given by way of example but not to be considered in a limitative sense, wherein:

FIG. 1 schematically represents a portion of a dental arch with an edentulous area;

Figure 1:
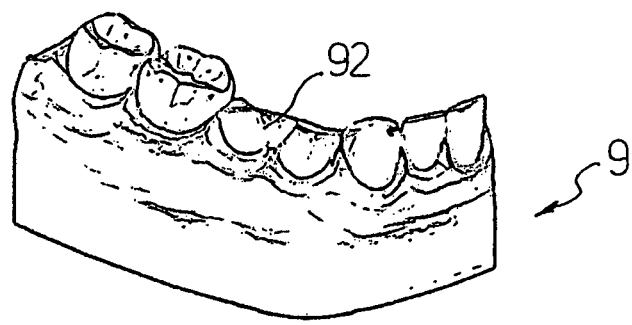
Figure 2A:
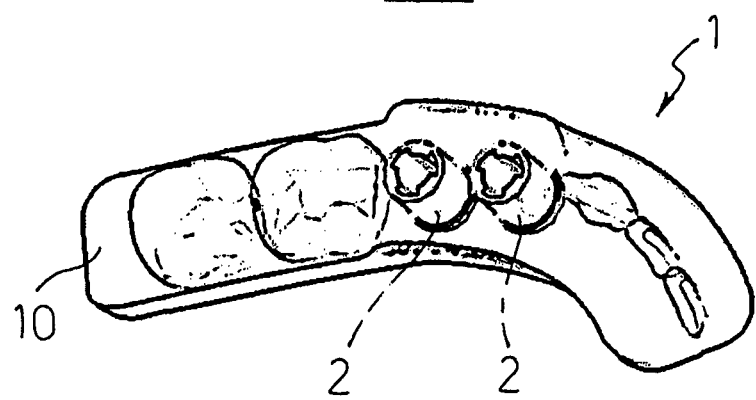
FIG. 2A is a bottom perspective view of a surgical guide for dental implantology in accordance with the present invention and usable for the treatment of the dental arch of FIG. 1.
Figure 2B:
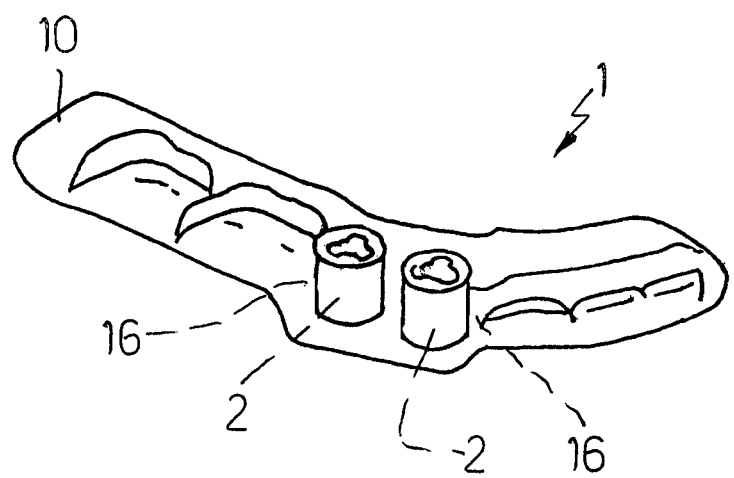
FIG. 2B represents a top perspective view of the surgical guide of FIG. 2A.
Figure 3A:
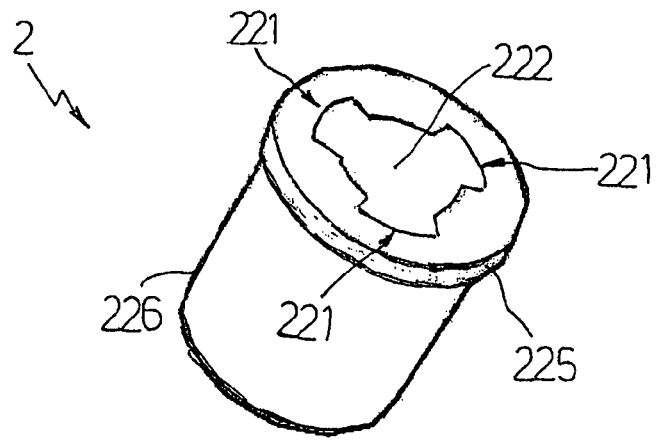
FIG. 3A is a side perspective view of a sleeve used in the surgical guide of FIG. 2A and FIG. 2B.
Figure 3B:
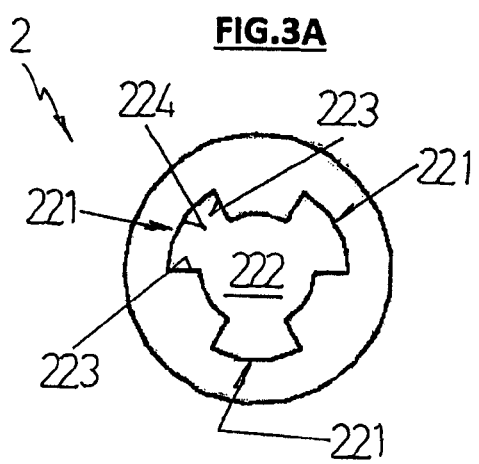
Figure 3C:
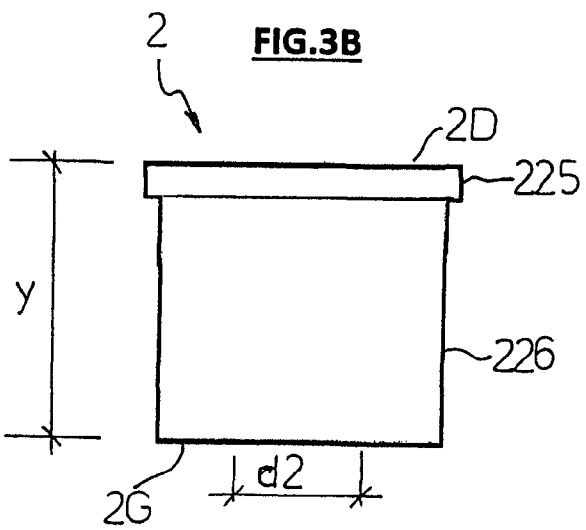
Figure 4:
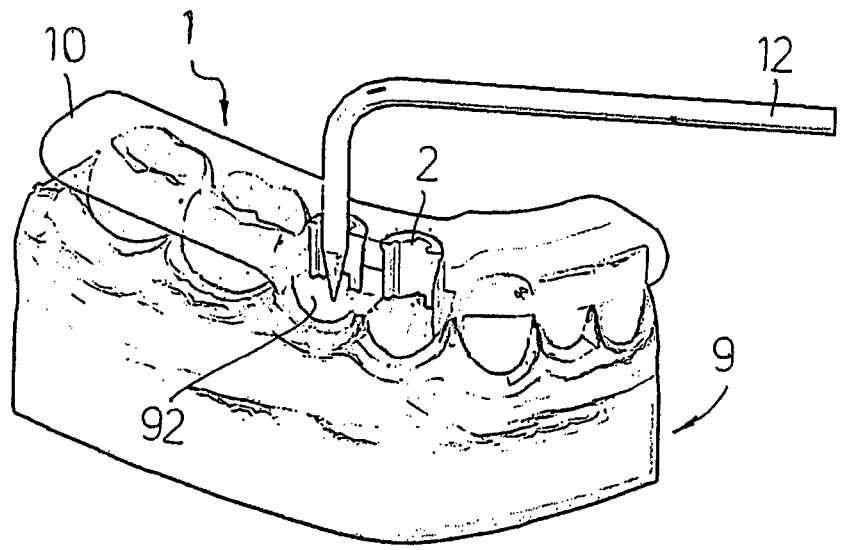
Figure 5:
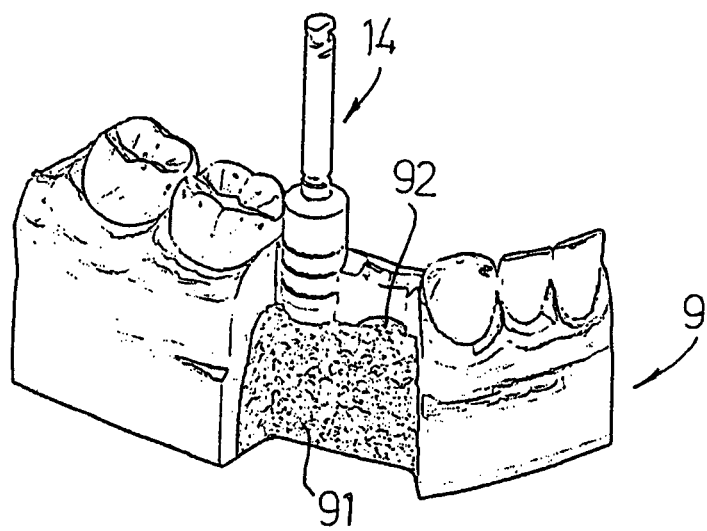
Figure 6:
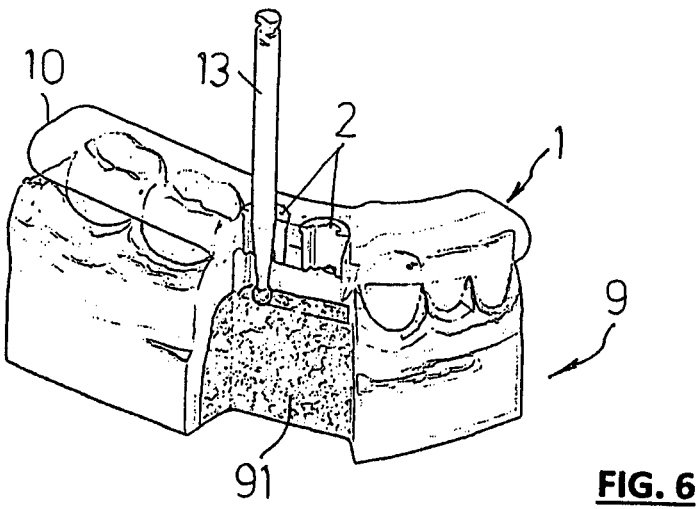
Figure 7A:
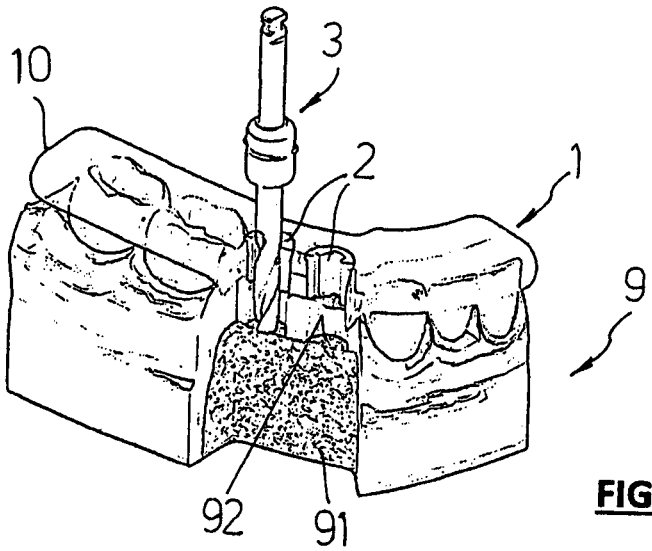
Figure 7B:
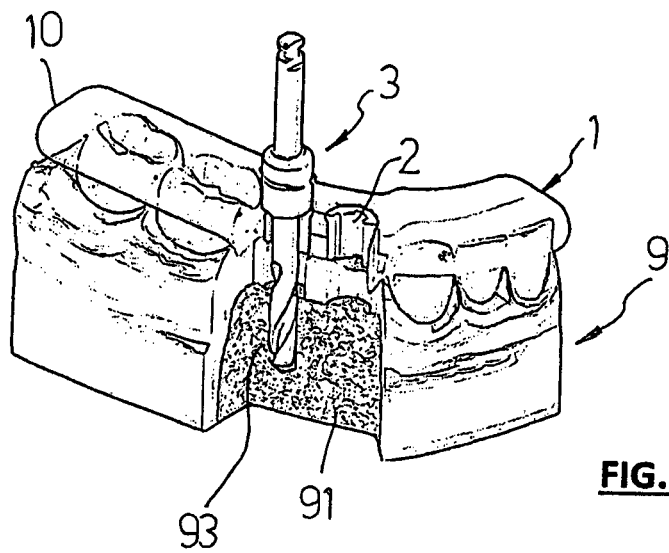
Figure 8A:
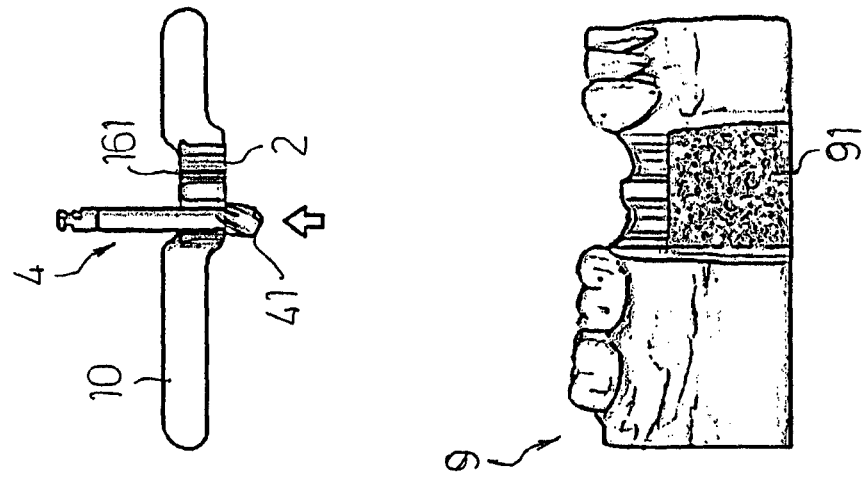
Figure 8B:
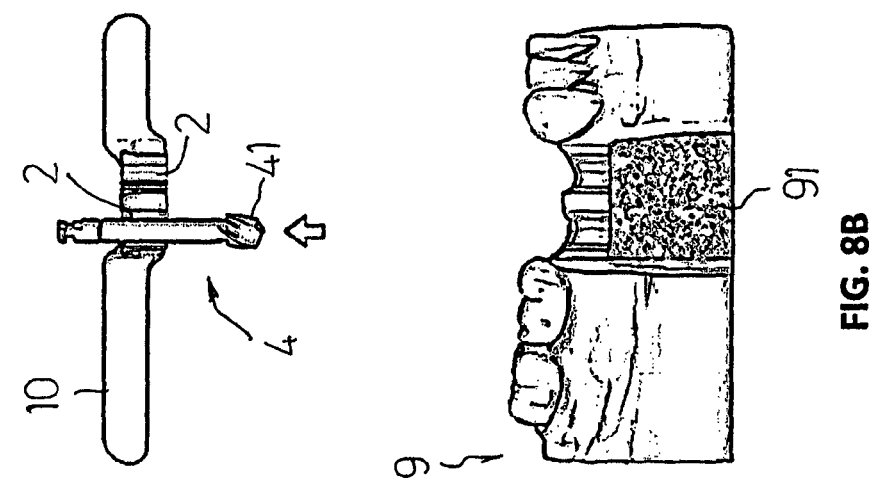
Figure 8C:
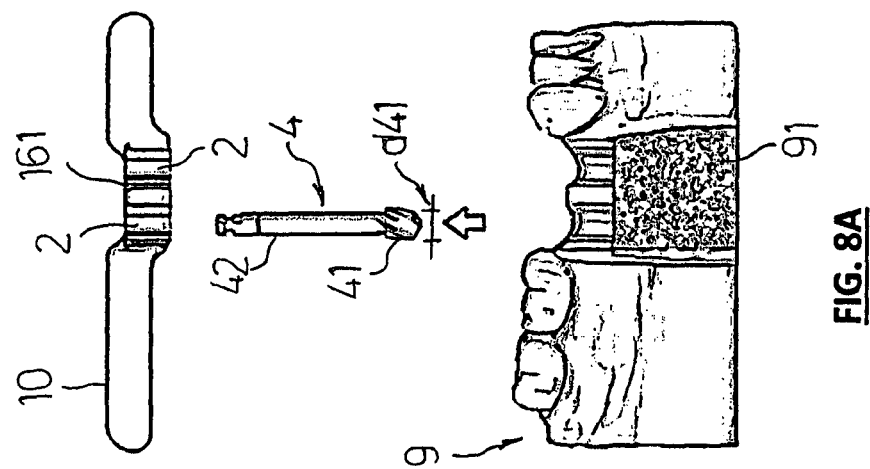
Figure 9A:
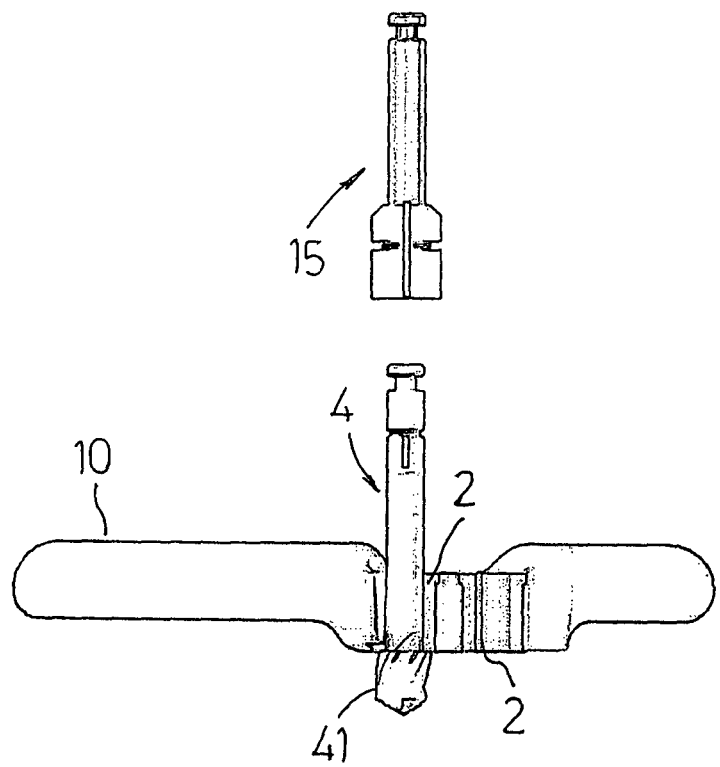
Figure 9B:
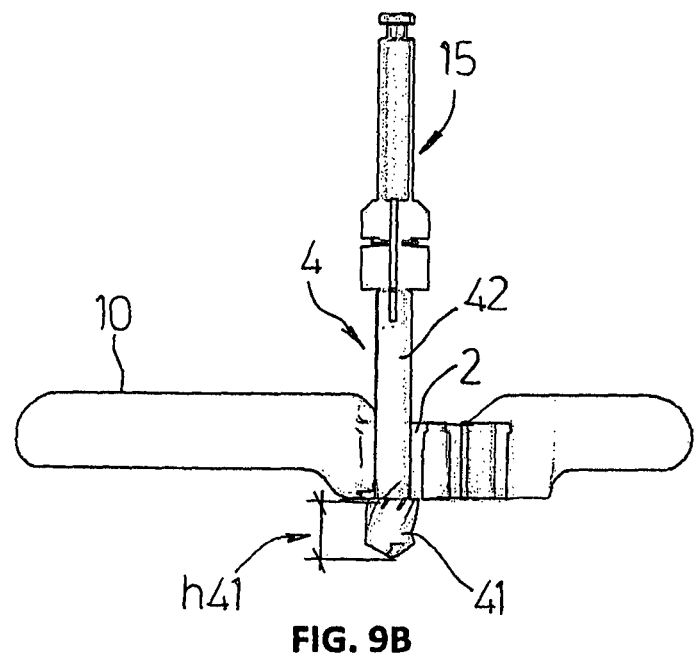
Figure 10C:
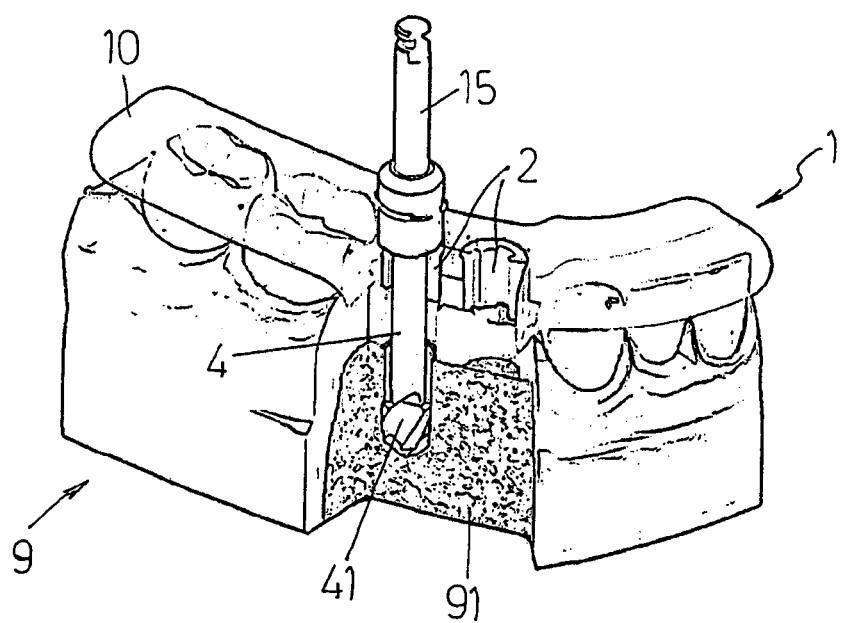
Figure 11C:
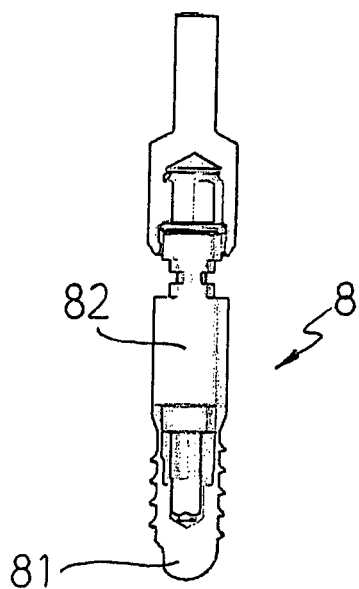
Figure 11A:
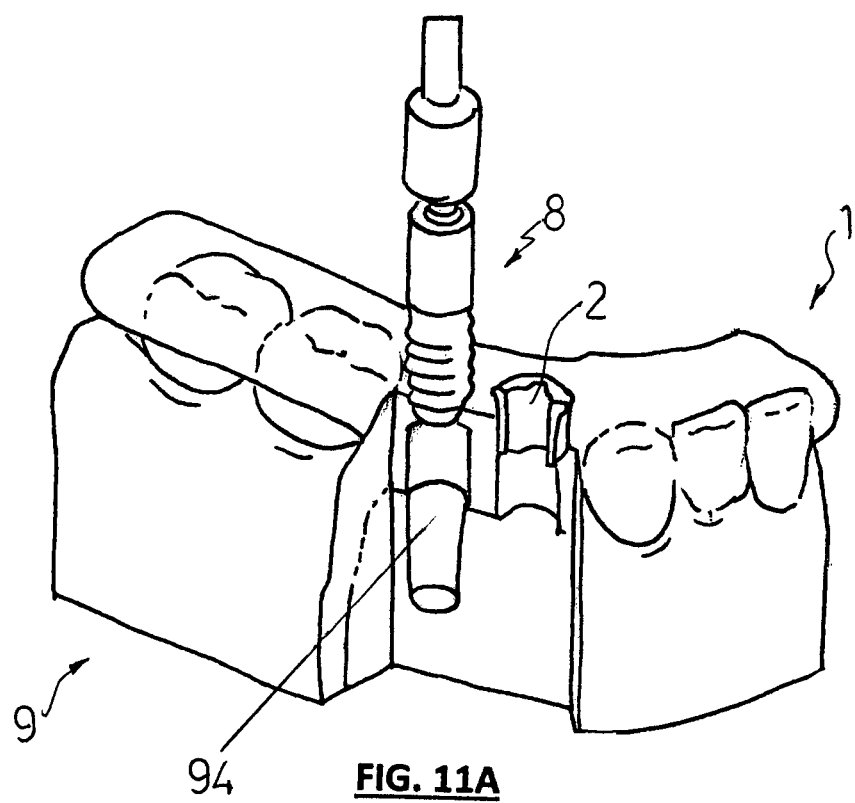
Figure 11B:
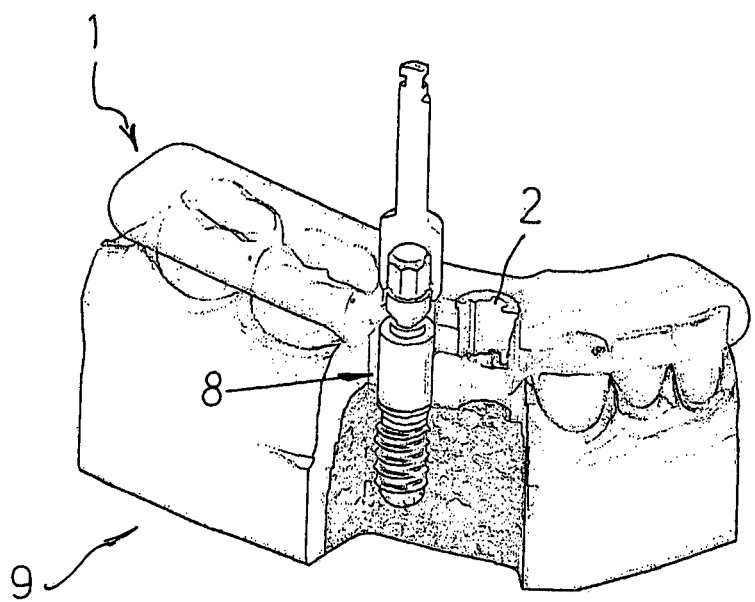
Figure 13:
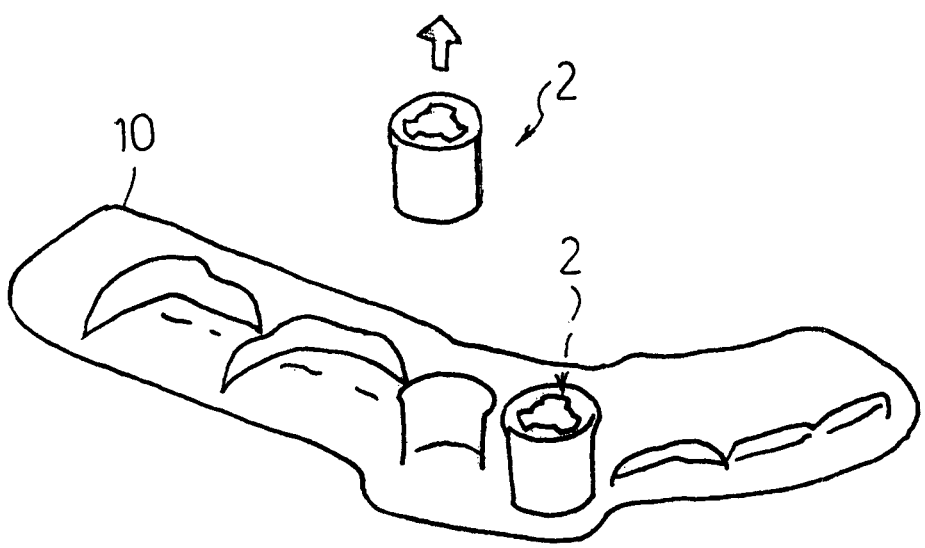

FIG. 3*b* represents a plan view of the sleeve of FIG. 3A;

FIG. 3C is a side view of the sleeve of FIG. 3A;

FIG. 4 represents the use of a probe with the surgical guide of FIG. 2A and FIG. 2B placed on the dental arch of FIG. 1;

FIG. 5 represents a phase of mucotomy performed with circular scalpel on the dental arch of FIG. 1;

FIG. 6 represents the use of a ball drill with the surgical guide of FIG. 2A and FIG. 2B placed on the dental arch of FIG. 1;

FIGS. 7A, 7B represent two operative steps concerning the use of a pilot drill with the surgical guide of FIG. 2A and FIG. 2B placed on the dental arch of FIG. 1;

FIGS. 8A-8C represent a sequence concerning the positioning of an enlarging drill on the surgical guide of FIG. 2A and FIG. 2B;

FIGS. 9A, 9B represent the connection of the shaft of the enlarging drill shown in the preceding figures with the driving head of a dental handpiece;

FIGS. 10A-10C represent a sequence concerning the use of the enlarging drill with the surgical guide of FIG. 2A and FIG. 2B placed on the dental arch of FIG. 1;

FIGS. 11A-11C represent the insertion of a dental implant on the dental arch of FIG. 1 through the surgical guide shown in FIGS. 2A and 2B;

FIGS. 12A-12D schematically show some phases of realization of the plate (10);

FIG. 13 schematically represents a possible step of removing a sleeve from the plate (10).

Reduced to its essential elements and with reference to the figures of the attached drawings, a surgical guide (1) for dental implantology in accordance with the present invention comprises, as shown in FIGS. 2A, 2B, a plate (10) in which are positioned two sleeves (2). The plate (10) consists of a component made of resin that can be realized, as further described below, starting from a model of the patient in correspondence of a dental arch with an edentulous area (9) where it is intended to place two fixtures (8) of dental implants, as further described below. The implants are of the type comprising an artificial root or fixture destined to engage the bone, and an abutment, insertable into the artificial root, on which it is possible to fix the prosthetic tooth. The insertion points and orientation of the fixtures of the implant (8) can be established by means of diagnostic tests and computerized elaborations of diagnostic tests known per se (further described below). The sleeves (2) are positioned and oriented in the plate (10) in such a way that, by using the surgical guide (1), it is possible to insert, as described further below, the fixtures of the implant (8) into the bone (91) according to insertion points and orientations provided by the diagnostic tests. Each of the sleeves (2) has an occlusal side (2D) and a gingival side (2G). In the illustrated examples, the occlusal side (2D) is the upper one, while the gingival side (2G) is the lower one.

Figure 12A:
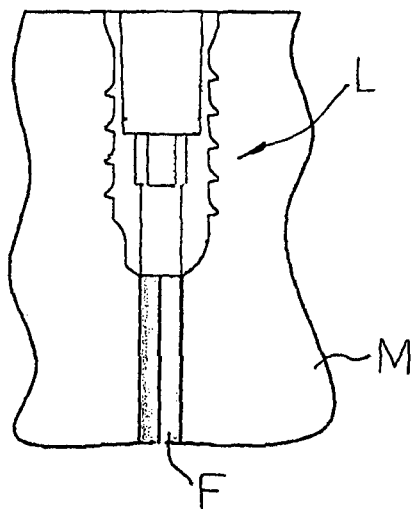
Figure 12B:
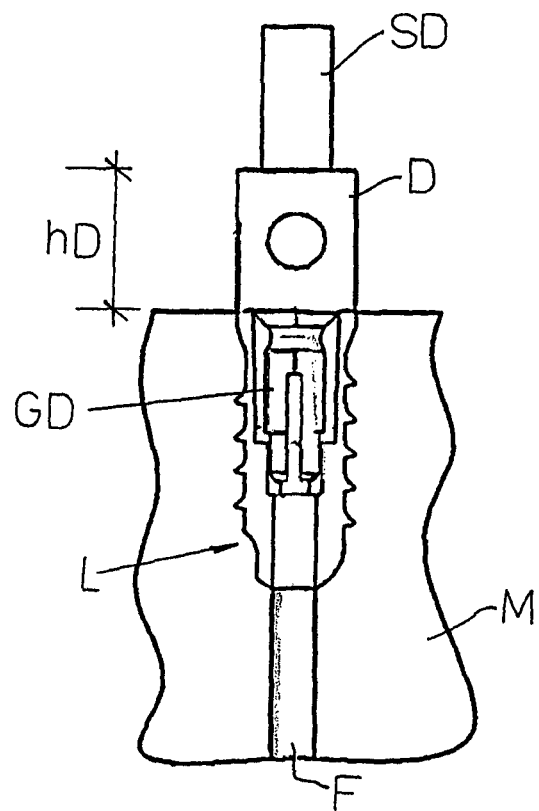
Figure 12C:
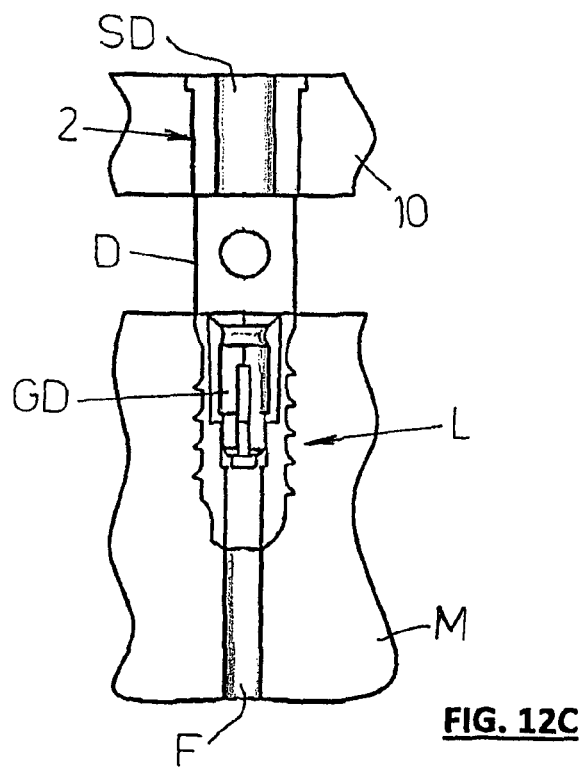
Figure 12D:
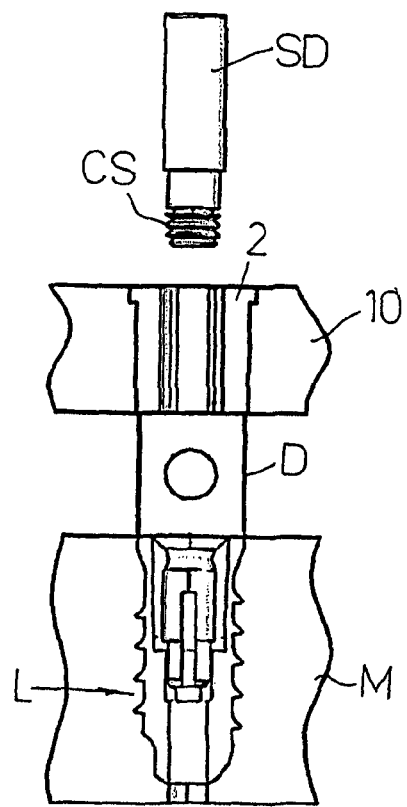

FIGS. 12A-12D schematically show a possible way of making the plate (10). FIG. 12A shows a portion of the model (M) of the bone structure of the dental arch—obtainable, for example, by processing data and diagnostic images with the software "3Diagnosys" of the Italian company 3Diemme combined with a 3D printer for rapid prototyping—with holes and seats for simil-fixtures, or so-called "laboratory" dental implants (L) having the same size and shape of those destined to be inserted in the bone of the patient's dental arch but made of a different material. The orientations of the holes or seats for the laboratory implants (L) are determined by the doctor depending on the specific anatomy of the dental arch detected in the diagnostic phase. The model (M) is also provided with lower holes (F) in correspondence of the laboratory implants (L) to enable to insert a rod (not shown) therein in order to extract, by pushing them from the bottom upwards, the abutments inserted in the same implants (L) during the steps of customizing the same abutments (not shown in the drawings). Starting from the model (M) in the configuration of FIG. 12A, a spacer is placed on each laboratory implant (L). More precisely, as shown in FIG. 12B, the spacer has a shank (GD) that is inserted into the cavity of the laboratory implant (L), a cylindrical middle part (D) intended to be with its lower base in contact with the upper base of the laboratory implant (L), and an upper cylindrical part (SD), of smaller diameter than the middle part (D), having a threaded shank (CS) screwed in the middle part (D). The height (hD) of said middle part (D) is greater than the height (h41) of the cutting head of the drill (4) described below. For example, hD=5 mm. Then, on the said upper part (SD) a sleeve (2) is positioned, as shown in FIG. 12C, after which it is formed the plate (10) with self-curing resin of the type normally used in this field. Subsequently, the above-mentioned upper part (SD) is unscrewed from the middle part (D) and extracted through the sleeve (2) incorporated in the resin of the plate (10) thus realized. Finally, the technician finishes the plate (10) according to the anatomy of the dental arch, using tools, such as drills and the like, as normally occurs in order to realize the surgical guides for dental implantology.

Since the said lower, median and upper parts (GD, D, SD) are coaxial with each other, the orientation of the sleeve (2) in the plate (10) coincides exactly with that of the laboratory implant (L) as the sleeve (2)—during the polymerization of the resin—is fitted on the upper part (SD) which is coaxial to the lower part (GD) inserted in the laboratory implant (L) and, therefore, constitutes an extremely precise guide. In other words, since the plate (10) is built around the sleeve (2) precisely oriented as the laboratory implant (L) which in turn is oriented as decided by the physician, during the steps (described below) of use of the plate (10) there is the maximum precision in the orientation of the dental implant into the bone of the patient. Each bush (2), visible in particular in FIGS. 3A-3C, has a tubular body (226) of predetermined diameter with an upper collar (225) having a diameter greater than the same body (226). In addition, the sleeve (2) is crossed centrally and longitudinally by a cylindrical bore (222) of predetermined diameter with three side sectors (221) identical to each other. Each sector (221) consists of a cavity cut laterally to the central hole (222) and delimited by a cylindrical surface portion (224) between two radial surfaces (223). The cylindrical surfaces (224) which delimit the sectors (221) are concentric both among themselves and with respect to the central hole (222). Furthermore, the symmetry planes of the three sectors (221), which intersect in the longitudinal axis of the sleeve (2), are arranged at 120° relative to one another.

The central hole (222) and the lateral compartments (221) are communicating. In the accompanying drawings, the sleeves (2) stay in the plate (10) with the collar (225) facing up. In the realization phase of the plate (10) previously described, each bush (2) results in a corresponding cylindrical seat-through (16) with predetermined length and orientation and a diameter equal to that of the body (226) of the same sleeve (2). The said cylindrical seat (16) is delimited at the top by a flat surface (161), visible in particular in FIGS. 8A-8C, perpendicular to the longitudinal axis of the same seat (16). In practice, the lower surface of the collar (225) is in abutment against the corresponding surface (161) of the plate (10). When it is mounted on the dental arch (9), the surgical guide (1) is spaced from the bone (91), in correspondence of each bush (2), of a predetermined value.

The height (y) of each bush (2), by way of example, may be 5 mm. Once positioned the surgical guide (1) on the dental arch (9), each sleeve (2) constitutes a useful guide for guiding a drill (3, 4) during the operation of osteotomy. The sectors (221) of the sleeve (2) are useful for the passage of a liquid for cooling the drill (3, 4) and then the bone.

Before using the surgical guide (1), it is carried out a mucotomy with a circular scalpel (14) to remove a portion of the gum at the point of insertion of the implant (8) into the bone (91), as shown in FIG. 6. The points (92) where the mucotomy must be executed are identified by means of a probe (12) and/or a round or ball drill (13). In practice, the surgical guide (1) is positioned on the dental arch (9) and therefore are the said points (92) marked on the gum by passing the probe (12) and/or the round drill (13) through the sleeves (2) and the gum is incised. In order to perform the mucotomy, the surgical guide (1) is removed.

After the mucotomy, the osteotomy is carried out by positioning the surgical guide (1) on the dental arch (9). For a more precise execution of the bore (94) for the implant (8), it can first be practiced a pre-bore (93) with a pilot drill (3), which is then expanded with a step drill (4) as described below. Each drill (3, 4) is driven via a driver (6) by a handpiece (not shown) to which it is connected through its shank (42).

The pilot drill (3) is inserted in each sleeve (2) of the surgical guide (1) and made to advance for a predetermined stroke in the bone (91), as shown in FIGS. 7A and 7B, thus realizing a number of pre-bores (93) equal to the number of implants to be applied, each of predetermined depth and diameter. The pilot bores (93) are then expanded with the step drill (4) thus completing the osteotomy.

If the bone is not particularly hard, the pre-drilling is not required and the doctor uses only the step drill (4).

The step drill (4) is first associated with the surgical guide as shown in FIGS. 8A-8C. In practice, the surgical guide (1) is removed from the dental arch (9) and the step drill (4) is inserted from the bottom in one of the sleeves through its shank (42).

The shank (42) of the step drill (4) is inserted into the central hole (222) of a sleeve (2) until the top of the head (41) of the drill (4) is in contact with the bottom edge of the same sleeve (2), as shown in FIG. 8C. The diameter of the head (41) of the milling step (4) is in fact greater than the diameter of the hole (222, 221) of the sleeve (2). Then, holding the step drill (4) in position, the surgical guide (1) is placed on the dental arch (9). Since the head (41) of the step drill (4) has a height (h41) lower than or equal to the height of the space (100) present between the surgical guide (1) and the bone in the concerned edentulous area, the head (41) of the step drill (4) is placed in the same space (100). So positioned, the milling step (4) is connected to the driver (6) through the respective shank (42) and made to advance to a predetermined depth in the bone (91), as shown in FIGS. 10B and 10C.

Preferably the said height (h41) has a value less than or equal to 5 mm. The step drill (4) is positioned and used with the other sleeves (2) as previously said, thus realizing a number of bores (94) equal to that of the implants (8) to be inserted into the bone (91) and each of fixed depth, orientation and diameter.

It is therefore clear that, for the same operating space in the mouth of the patient, the maximum depth of the bore (94) is greater than that of a bore obtained with the traditional method, i.e. obtained by inserting the drill (4) from the outside of the surgical guide (1) and not pre-positioning it from the bottom side of the latter intended to face the dental arch in the operational phase. In other words, the maximum depth of the bore (94) is increased, compared to the depth of a bore achievable with the traditional method, of a value equal to the height (y) of the sleeve (2) increased by the height (hD) of said spacer (D). For example, with y=5 mm and hD=5 mm, this increase (y+hD) is 10 mm. In practice, according to the present invention, the void (100) in the surgical guide, that according to example described above is created by the middle part of the said spacer, is high enough to accommodate the drilling head of the drill, so that the surgical guide can be seated in correct position before starting to drill.

Thereafter, each sleeve (2) is removed by pulling it out from the plate (10) as shown in FIG. 13, to insert, into the corresponding bore (94) practiced in the bone (91), the respective dental implant (8) through the same plate (10). In this way the implant (8) is guided during its insertion. The positioning of the dental implant (8) into the bone (91) is shown in FIGS. 11A and 11B.

The dental implant (8) is of the traditional type, i.e. of the type having a threaded fixture (81) to be screwed into the bore (94) made in the bone (91) and an abutment (82) destined to be associated with the fixture (81).

Since, compared to the traditional method, the depth of the bore (94) is greater, under equal conditions, even the implant (8) may be longer. Therefore, the durability and stability of the implant (8) inserted into the bone (91) using a surgical guide for dental implantation (1) according to the present invention instead of a traditional surgical guide are higher.

In practice, the construction details may vary in any equivalent way as regards the single described and illustrated elements, without nevertheless departing from the scope of the adopted solution idea and thereby remaining within the limits of the protection granted to the present patent.

The invention claimed is:

1. A method for making a guide surgical system for dental implantology, the method comprising:
   producing a plate provided with at least one guide sleeve delimiting a corresponding through hole of which an axis is oriented according to a predetermined direction, and
   producing a model of anatomical structures that underlie a dental arch or part of a dental arch by means of electronic processing of diagnostic images, in which said model exhibits holes oriented according to a given angle, in each of said holes being inserted a laboratory implant;
   wherein, the step of producing a plate comprises:
      placing a spacer on each said laboratory implant, the spacer being provided with:
         a shank inserted into a cavity of the laboratory implant,
         a cylindrical middle part having a lower base contacting an upper base of the laboratory implant, and
         a cylindrical upper part having a diameter less than a diameter of the cylindrical middle part and a threaded stem screwed in said cylindrical middle part, wherein a height of said cylindrical middle part is greater than a height of a drilling head of a drill for osteotomy;
      placing said at least one guide sleeve on the cylindrical upper part,
      placing self-curing resin around said at least one guide sleeve to form said plate with said at least one guide sleeve incorporated therein; and
      when curing of the self-curing resin is completed, unscrewing said upper cylindrical part from said cylindrical middle part and extracting said upper cylindrical part through said at least one guide sleeve.

2. A method according to claim 1, wherein said height of said cylindrical middle part is 5 mm and said height of said drilling head of said drill is less than 5 mm.

* * * * *